United States Patent
Akpinar et al.

(10) Patent No.: US 10,561,449 B2
(45) Date of Patent: Feb. 18, 2020

(54) HUMERUS INTERNAL SAFE LOCKING NAIL

(71) Applicant: TST RAKOR VE TIBBİ ALETLER SANAYİ VE TİCARET LİMİTED ŞİRKETİ, Pendik-Istanbul (TR)

(72) Inventors: Fuat Akpinar, Üsküdar-Istanbul (TR); Ahmet Fethi Polat, Pendik-Istanbul (TR)

(73) Assignee: TST RAKOR VE TIBBI ALETLER SANAYI VE TICARET LIMITED SIRKETI, Pendik-Istanbul (TR)

( * ) Notice: Subject to any disclaimer, the term of this patent is extended or adjusted under 35 U.S.C. 154(b) by 0 days.

(21) Appl. No.: 15/766,596

(22) PCT Filed: Oct. 21, 2016

(86) PCT No.: PCT/TR2016/050393
§ 371 (c)(1),
(2) Date: Apr. 6, 2018

(87) PCT Pub. No.: WO2017/069719
PCT Pub. Date: Apr. 27, 2017

(65) Prior Publication Data
US 2018/0296258 A1 Oct. 18, 2018

(30) Foreign Application Priority Data

Oct. 21, 2015 (TR) .................................. 2015/13147

(51) Int. Cl.
*A61B 17/72* (2006.01)
*A61B 17/68* (2006.01)

(52) U.S. Cl.
CPC .......... *A61B 17/7266* (2013.01); *A61B 17/72* (2013.01); *A61B 17/725* (2013.01); *A61B 17/7233* (2013.01); *A61B 2017/681* (2013.01)

(58) Field of Classification Search
CPC . A61B 17/7266; A61B 17/72; A61B 17/7233; A61B 17/725; A61B 2017/681
(Continued)

(56) References Cited

U.S. PATENT DOCUMENTS 2,490,364 A * 12/1949 Livingston ............. A61B 17/68
606/68
3,759,257 A * 9/1973 Fischer .............. A61B 17/7266
606/63
(Continued)

FOREIGN PATENT DOCUMENTS

WO 2014035811 A1 3/2014

*Primary Examiner* — Pedro Philogene
*Assistant Examiner* — David C Comstock
(74) *Attorney, Agent, or Firm* — Oppenhuizen Law PLC; David L. Oppenhuizen

(57) ABSTRACT

An intramedullary nail for surgically repairing a fractured humerus. The nail has a locking pin extending within the inside of the nail. The locking pin locks the nail into the distal portion of a humerus. The nail has an upper part which includes a compression hole, a locking pin slot, and angled screw holes. The nail is locked into the distal end of the humerus bone by screwing a bone-entering tip of the locking pin on the threaded end of the locking pin. The locking pin can be moved with a screwdriver from inside in order to extend the lower part of the pin out of the distal hole. The lower part of the humerus internal locking nail includes a rotation preventive end structure of the nail, and an angled tip on the distal part of the nail.

8 Claims, 1 Drawing Sheet

(58) Field of Classification Search
USPC .............................................. 606/62, 63, 68
See application file for complete search history.

(56) References Cited

U.S. PATENT DOCUMENTS

| | | | | |
|---|---|---|---|---|
| 4,091,806 | A * | 5/1978 | Aginsky | A61B 17/7225 606/63 |
| 5,814,047 | A | 9/1998 | Emilio et al. | |
| 5,971,986 | A * | 10/1999 | Santori | A61B 17/7266 606/323 |
| 6,270,499 | B1 | 8/2001 | Leu et al. | |
| 8,337,495 | B1 * | 12/2012 | Powlan | A61B 17/7266 606/62 |
| 8,449,583 | B2 * | 5/2013 | Krebs | A61B 17/7266 411/32 |
| 2002/0165544 | A1 * | 11/2002 | Perren | A61B 17/7266 606/63 |
| 2004/0010255 | A1 | 1/2004 | Warburton | |
| 2014/0066932 | A1 * | 3/2014 | Appenzeller | A61B 17/1725 606/64 |

* cited by examiner

HUMERUS INTERNAL SAFE LOCKING NAIL

FIELD OF THE INVENTION

The present invention pertains to intramedullary nails which are used in the surgical treatment of humerus fractures.

DESCRIPTION OF THE PRIOR ART

The humerus is located between the scapula and the olecranon and forms the bone structure of the upper arm region. The humerus is often broken by direct impact and by axial loading from elbow direction. Humeral (arm) fractures are commonly seen. In fact, one of every 20 fractures is a humeral fracture of the arm, and they are often seen in traffic accidents or as a result of falling onto the hands in an accident.

Intramedullary nails can be used for the surgical treatment of humeral fractures. When an intramedullary nail is used, the patient is exposed to lots of radiation when a guide or fluoroscopy is needed to lock the distal end of the intramedullary nail into the bone.

In addition, another disadvantage of the intramedullary nails in the prior art is that they require an extra skin incision at the distal part of the humerus. This additional incision increases the risk of infection at the incision site.

For example, Chinese patent application number CN104323847 discloses a locking nail, or intramedullary nail, used to treat and fix humeral fractures. But the disclosure of CN104323847 does not solve the problems discussed herein since it is still necessary to make the incision at the distal end of the upper arm to lock the distal end of the intramedullary nail in position.

As a result, there is an increased risk of infection, probable injuries to the radial nerve, median nerve, and musculocutaneous nerve near the distal end of the nail, in addition to extended healing time.

SUMMARY OF THE INVENTION

An object of the invention is to develop a humerus internal safe locking nail to eliminate the negativities of existing nails in the prior art, which will result in faster and more effective solutions to treating humerus fractures.

Another object of the invention is to lock the distal end of the nail from inside out to avoid having to make an incision at the distal and of the upper arm. In this way, all the problems are avoided that may arise from cutting an incision to lock the distal end of the nail in place.

Another object of the invention is to simplify and shorten the surgical procedure for installing the intramedullary nail.

Yet another object of the invention is the elimination of possible damage to the radial nerve, median nerve, and musculocutaneous nerve near the distal end of the upper arm.

The humerus internal safe locking nail described herein below provides many advantages and is capable of achieving the objectives mentioned above.

For a more complete understanding of the present invention, reference is made to the following detailed description and accompanying drawings. In the drawings, like reference characters refer to like parts throughout the views in which:

DESCRIPTION OF THE REFERENCE NUMERALS

| | |
|---|---|
| 1 | Humerus internal locking nail (Humerus insafelock Nail) |
| 2 | Locking pin |
| 3 | Locking pin sending slot |
| 4 | Compression hole of the nail |
| 5 | Locking pin slot of the nail |
| 6 | Angled screw holes on the proximal of nail |
| 7 | Threaded end of the locking pin |
| 8 | distal hole of the nail |
| 9 | Bone entering tip of the locking pin |
| 10 | Anatomically angled tip on the distal part of the nail |
| 11 | Threaded proximal part of the locking pin |
| 12 | Rotation preventive end structure of the nail |
| 13 | Upper part |
| 14 | Lower part |
| 15 | Screw holes on the proximal of the nail |

DETAILED DISCLOSURE OF THE INVENTION

Figure 1:
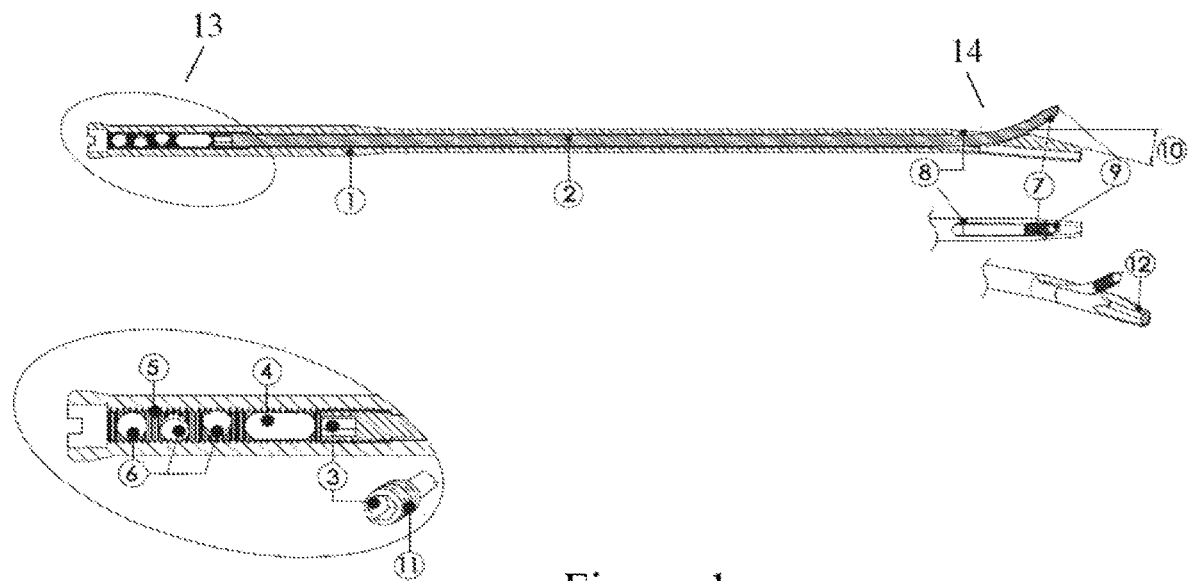
FIG. 1 is a sectional view of a first embodiment of the present invention hereof.
Figure 2:
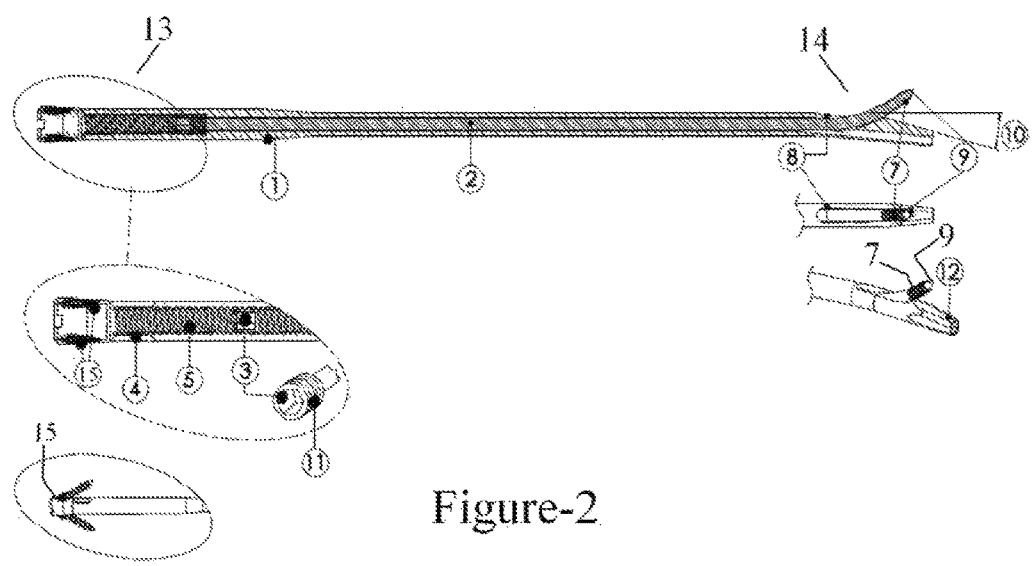
FIG. 2 is a sectional view of a second embodiment of the present invention hereof.

In accordance with the present invention and as shown in FIGS. 1 and 2, there is provided a humerus internal locking nail (1) having a locking pin (2) extending within and mounted on the inside of the humerus internal locking nail (1). The locking pin (2) provides for locking of the humerus internal locking nail (1) at the distal portion of the humerus. The humerus internal locking nail (1) has an upper part (13) which includes a compression hole of the nail (4), a locking pin slot of the nail (5), and angled screw holes on the proximal end of the nail (6). The humerus internal locking nail (1) is locked into the distal end of the humerus bone by screwing, or rotating, the bone-entering tip of the locking pin (9) on the threaded end of the locking pin (7). The locking pin (9) can be moved with a screwdriver from inside on the locking pin (2) over the locking pin sending slot (3) in order to extend the lower part (14) out of the distal hole of the nail (8). The lower part (14) of the humerus internal locking nail (1) includes a rotation preventive end structure of the nail (12). There is also provided an anatomically angled tip on the distal part of the nail (10) defined between the rotation preventive end structure of the nail (12) and the bone-entering tip of the locking pin (9).

The humerus internal locking nail (1) comprises any suitable material type which is well-known in the art for use with intramedullary nails. However, it is inherent from the disclosure herein that the locking pin (9) is formed from a flexible or bendable material since the bent portion of the locking pin (9) must necessarily be able to rotate (and thus continue to bend) when the locking pin (9) is rotated to be advanced out of the distal hole of the nail (8). Therefore, the locking pin (9) is comprised of any suitable bendable material, such as a bendable metal alloy, a non-rigid polymeric material, a coiled spring, and so forth.

The humerus internal locking nail (1) can be used to treat proximal humerus and diaphyseal (shaft) humerus fractures. The humerus internal locking nail (1) provides advantages over the prior art. For example, the humerus internal safe locking nail (1) can be used on either the left or right humerus. The humerus internal safe locking nail (1) can also be placed close to the most distal location on the humerus above the olecranon fossa.

As described below, the humerus internal locking nail (1) eliminates the need for fluoroscopy to lock the distal end of the humerus internal locking nail (1) into the distal end of the humerus. As is well-known in the art, fluoroscopy is an imaging technique that uses x-rays. Thus, the humerus internal locking nail (1) eliminates radiation exposure to the patient, along with the adverse effects thereof, which would otherwise be present with intramedullary nails in the prior art.

The distal end of the nail is not locked into the distal end of the humerus like the known classic systems in which screws extend through screw holes in the nail. Rather, the distal locking of the humerus internal locking nail (1) is accomplished by screwing from inside to outside of the nail (1). As a result, there is no skin incision at the distal end of the humerus to lock the distal part of humerus. This provides aesthetic advantages by avoiding additional incisions. But even more so, there are important functional advantages by avoiding muscle, tendon, and fascia damage during surgery. Furthermore, radial nerve, median nerve, and musculocutaneous nerve injuries which are often seen at the distal locking in the prior art are eradicated. Lastly, the duration of the surgical procedure is shortened.

In use, the humerus internal locking nail (1) is used as follows:

After the fractured humerus has been set into the correct anatomic position, then the humerus internal locking nail (1) is inserted from the appropriate entrance into the medullary cavity of the bone. The humerus internal locking nail (1) is extended through the fracture line until it reaches its end position, which is the most distal part end about 25 mm over the olecranon fossa. Because the humerus internal locking nail (1) is a long nail, it is placed along the humerus canal.

While the humerus internal locking nail (1) is placed, the anatomically angled tip on the distal part of the nail (10) is oriented toward the anterior face of the humerus (front face of humerus). The angled tip on the distal part of the nail (10) is between 5°-40°. The anatomically angled tip on the distal part of the nail (10) and the rotation preventive end structure (12) of the nail (1) provides an easy movement of the humerus internal locking nail (1) through the medullary cavity to the distal end thereof, but also prevents rotational movement which would otherwise occur.

When the humerus internal locking nail (1) is placed into the medullary cavity in this way, the locking pin (2) is then extended out of the distal hole of the nail (8) by using the locking pin sending slot (3).

The bone-entering tip of the locking pin (9) is a sharp tip on the threaded end of the locking pin (7) that has the ability to enter the bone. The bone-entering tip of the locking pin (9) is extended out from the distal hole of the nail (8) at the distal end of the humerus internal locking nail (1). The bone-entering tip of the locking pin (9) is angled preferably 20-60 mm above the distal end so that it enters at the posterior (back) side into the bone and locks by screwing. The threaded end of the locking pin (7) is on the locking pin (2) and makes it easier to progress the bone-entering tip of the locking pin (9) forward into the humerus.

The desired tight fixation at the distal end of the humerus bone is obtained by screwing the locking pin (2) into the bone. The locking pin (2) extends out from the distal hole of the nail (8) at the distal end of the humerus internal locking nail (1) toward the posterior (back) direction, and presses the anatomically angled tip of the distal part of the nail (10) toward the anterior (front) of the humerus. The anatomically angled tip of the distal part of the nail (10) is between 5°-40° at the lower part (14) of the humerus internal safe locking nail (1).

After the threaded end of the locking pin (7) is screwed posteriorly into the distal end of the humerus bone, the threaded proximal end of the locking pin (11) is locked into its final position there because it matches the locking pin slot (5) at the proximal end of the humerus internal safe locking pin (1).

If there is a need to close the gap between the fracture line in the humerus by compressing the ends of the humerus together during the proximal locking stage, then a compression screw is passed through the compression hole (4) of the humerus internal locking nail (1). The compression screw compresses the humerus to close the gap between the fracture line by sending the compression screw through the compression hole (4) of the top of the humerus internal locking nail (1). If necessary, the 0-20° oblique angled screw hole at the proximal end of the humerus internal locking nail (1) can be used.

According to a second embodiment hereof, and as shown in FIG. 2, the humerus internal locking nail (1) has an alternate structure pertaining to the upper part (13) on the proximal section of the nail. The description of use of the humerus internal locking nail (1) according to the second embodiment is the same as the embodiment described above with respect to locking the bone-entering tip of the locking pin (9) into the bone, however, the second embodiment hereof differs as follows.

As shown in FIG. 2, the proximal end of the humerus internal locking nail (1) includes angled screw holes on the proximal end of the nail (15). As shown in the drawings, the screw holes (15) are angled 0-30° with respect to the humerus internal locking nail (1). Screws are sent through the angled screw holes on the proximal end of the nail (15) at an angle to each other via the angled the screw holes on the proximal end of the nail (15) to lock the proximal end of the humerus internal locking nail (1) in position within the bone.

An additional benefit according to this embodiment is that the need of an additional skin incision at the proximal locking is eliminated because of the location of the screw holes on the proximal end of the nail (15) allows the screws to be inserted into the screw holes on the proximal end of the nail (15) at the same incision through which the humerus internal locking nail (1) is placed. As a result, additional damage to soft tissue like muscle, tendon, and fascia is prevented. Loosening, migration (moving to different locations), or irritation of the proximal locking screws are not seen. Functional and aesthetic advantages are obtained. Similar to the elimination of the incision at the distal end of the bone, eliminating any additional incisions at the proximal end also avoids the use of a fluoroscope that emits X-ray during use. As a result, the surgical time for the operation is shortened. After surgery significant improvements of the patient's rehabilitation time are also obtained.

In a preferred application of the invention, the humerus internal locking nail (1) includes the locking pin (2) that is positioned longitudinally inside the humerus internal locking nail (1). The locking pin (2) is screwed from the proximal end thereof and extends out from the distal hole of the nail (8). There is provided at least one locking pin sending slot (3) on the locking pin (2) to extend the locking pin (2) out of the distal hole of the nail (8) to lock the distal part of the locking pin (2). There is provided at least one locking pin slot of the nail (5) at the proximal end of the humerus internal locking nail (1) which advances the locking pin (2) inside the humerus internal locking nail (1). There is also at least one threaded proximal part of the locking pin (11) on the locking pin (2), at least one threaded end of the locking pin (7) that is locked by extending out from the distal hole of the nail (8) on the locking pin (2), at least one bone-entering tip of the locking pin (9) that is locked in position by entering the bone at an angle, an anatomically angled tip on the distal part of the nail (10) that is created in an angled and flattened structure at the distal part of the humerus internal locking nail (1), and a rotation preventive end structure of the nail (12) at the distal end of the humerus internal locking nail (1).

The locking pin sending slot (3) includes a bone-entering tip of the locking pin (9) which locks the nail (1) in position by screwing into the distal end of the humerus. Also, the threaded end of the locking pin (7) extends out through the distal hole of the nail (8) on the lower part (14) by proceeding, or advancing, on the slot with a screwdriver.

There is an anatomically angled tip on the distal end of the nail (10) curved to a 5°-40° angle which eases entry into the bone on the distal end of the humerus internal locking nail (1).

There are also angled screw holes on the proximal end of the nail (6) with 0-20° angle on the upper part (13) of the humerus internal safe locking nail (humerus insafe lock nail) (1).

There are screw holes on the proximal end of the nail (15) that are oriented 0-30° with respect to the nail (1), and provided screws are inserted into the screw holes on the proximal end of the nail (15) angular to each other on the upper part (13).

The compression hole of the nail (4) is formed to provide locking and compression to fractured parts of the bone on the upper part (13).

There is a locking pin slot of the nail (5) on the upper part (13) of the humerus internal locking nail (1) which provides a matched position for the threaded proximal end of the locking pin (11) with the threaded proximal part of the locking pin (11) on the locking pin (2).

There is also provided a threaded end of the locking pin (7) on the locking pin (2) which tightens the anterior side of the humerus at the lower part (14) of the humerus internal locking nail (1), and which permits the locking pin (2) to stick into the bone from the inside (i.e., through the medullary cavity) out angularly by outgoing from a distal hole of the nail (8) at the lower part (14) of the humerus internal locking nail (1) and provides angular locking.

Lastly, there is a rotation preventive end structure of the nail (12) on the anatomically angled tip on the distal end of the nail (10) which eases entry into the bone on the distal part (14) of the humerus internal locking nail (1).

It should be understood that the foregoing description is only illustrative of the aspects of the disclosed embodiments. Various alternatives and modifications can be devised by those skilled in the art without departing from the aspects of the disclosed embodiments. Accordingly, the aspects of the disclosed embodiments are intended to embrace all such alternatives, modifications, and variances that fall within the scope of the appended claims. Further, the mere fact that different features are recited in mutually different dependent or independent claims does not indicate that a combination of these features cannot be advantageously used, such as a combination remaining within the scope of the aspects of the disclosed embodiments.

What is claimed is:

1. A nail for use in the surgical treatment of humeral fractures in a humerus, the nail comprising:
 a locking nail having an elongated body that is straight and hollow and includes a proximal end and a distal end, the distal end of the locking nail having an angled tip that is disposed at an angle with respect to the elongated body, the distal end of the locking nail additionally having a hole in a wall of the elongated body;
 a locking pin disposed within the elongated body, the locking pin having a curved threaded end which extends through the hole in the elongated body, the threaded end being bent and angled away from the angled tip of the distal end of the locking nail, the locking pin having a threaded proximal end positioned near the proximal end of the nail, the threaded proximal end being positioned within the elongated body of the locking nail, whereby rotating the threaded proximal end of the locking pin advances the axial position of the locking pin in the locking nail and advances the threaded end in a direction away from the body of the locking nail.

2. The nail of claim 1 wherein the angled tip on the distal end of the locking nail is curved at an angle of 5°-40° from an axis of the elongated body to ease the entry of the nail into the humerus.

3. The nail of claim 1 including angled screw holes positioned on the proximal end of the locking nail, the angled screw holes being positioned at an angle of 0°-20° from an axis of the elongated body.

4. The nail of claim 1 including screw holes positioned on the proximal end of the locking nail, the screw holes being positioned at an angle of 0°-300° from an axis of the elongated body.

5. A nail for use in the surgical treatment of humeral fractures in a humerus, the nail comprising:
 a locking nail having an elongated body that is hollow along the entire length thereof and includes a proximal end and a distal end, the distal end of the locking nail having an angled tip that is disposed at an angle with respect to the elongated body, the distal end of the locking nail additionally having a hole in a wall of the elongated body;
 a locking pin disposed within the elongated body, the locking pin having a curved threaded end which extends through the hole in the elongated body, the locking pin having a threaded proximal end positioned near the proximal end of the nail, the threaded proximal end being positioned within the elongated body of the locking nail, whereby rotating the threaded proximal end of the locking pin advances the axial position of the locking pin in the locking nail and advances the threaded end in a direction away from the body of the locking nail.

6. The nail of claim 5 wherein the angled tip on the distal end of the locking nail is curved at an angle of 5°-40° from an axis of the elongated body to ease the entry of the nail into the humerus.

7. The nail of claim 5 including angled screw holes positioned on the proximal end of the locking nail, the angled screw holes being positioned at an angle of 0°-20° from an axis of the elongated body.

8. The nail of claim 5 including screw holes positioned on the proximal end of the locking nail, the screw holes being positioned at an angle of 0°-300° from an axis of the elongated body.

* * * * *